(12) United States Patent
Prandi et al.

(10) Patent No.: US 8,414,583 B2
(45) Date of Patent: Apr. 9, 2013

(54) RESORPTIVE INTRAMEDULLARY IMPLANT BETWEEN TWO BONES OR TWO BONE FRAGMENTS

(75) Inventors: Bernard Prandi, Rennes (FR); Marc Augoyard, Tassin la Demi Lune (FR); Thomas Ledermann, Eschenbach (CH); Tristan Meusnier, Saint-Etienne (FR); Jacques Peyrot, Tassin la Demi Lune (FR); Judith Fellmann, Stafa (CH)

(73) Assignee: Memometal Technologies (FR)

( * ) Notice: Subject to any disclaimer, the term of this patent is extended or adjusted under 35 U.S.C. 154(b) by 0 days.

(21) Appl. No.: 12/918,105

(22) PCT Filed: Sep. 2, 2009

(86) PCT No.: PCT/FR2009/051658
§ 371 (c)(1),
(2), (4) Date: Oct. 29, 2010

(87) PCT Pub. No.: WO2010/029246
PCT Pub. Date: Mar. 18, 2010

(65) Prior Publication Data
US 2011/0144644 A1 Jun. 16, 2011

(30) Foreign Application Priority Data
Sep. 9, 2008 (FR) ...................... 08 56035

(51) Int. Cl.
*A61B 17/56* (2006.01)
*A61F 2/42* (2006.01)

(52) U.S. Cl.
USPC ...... 606/62; 623/21.11; 623/21.15; 623/21.19

(58) Field of Classification Search ............ 606/62, 606/63, 65–67, 76, 77, 86 R, 300, 301, 305, 606/307, 308, 319; 623/21.11, 21.15–21.17, 623/21–19, 23.39, 21.9
See application file for complete search history.

(56) References Cited

U.S. PATENT DOCUMENTS

| 3,462,765 A | 8/1969 | Swanson |
| 3,466,669 A | 9/1969 | Flatt |
| 3,593,342 A | 7/1971 | Niebauer et al. |
| 3,681,786 A | 8/1972 | Lynch |

(Continued)

FOREIGN PATENT DOCUMENTS

| EP | 1300122 A2 | 4/2003 |
| EP | 1923012 A1 | 5/2008 |

(Continued)

OTHER PUBLICATIONS

International Search Report for PCT/FR2008/050453 dated Nov. 4, 2008.

(Continued)

*Primary Examiner* — Ellen C Hammond
(74) *Attorney, Agent, or Firm* — Lerner, David, Littenberg, Krumholz & Mentlik, LLP

(57) ABSTRACT

The invention relates to an intramedullary implant for use between two bones or two bone fragments. The implant includes a single-piece body having a generally elongate shape and having, at each end, areas for anchoring to the bone portions in question, characterized in that one of said areas has a generally cylindrical shape while the other area has a flat cross-section.

18 Claims, 4 Drawing Sheets

U.S. PATENT DOCUMENTS

| | | | |
|---|---|---|---|
| 3,739,403 A | 6/1973 | Nicolle | |
| 3,824,631 A | 7/1974 | Burstein et al. | |
| D243,716 S | 3/1977 | Treace et al. | |
| 4,204,284 A | 5/1980 | Koeneman | |
| 4,276,660 A | 7/1981 | Laure | |
| 4,364,382 A | 12/1982 | Mennen | |
| D277,509 S | 2/1985 | Lawrence et al. | |
| D277,784 S | 2/1985 | Sgarlato et al. | |
| D284,099 S | 6/1986 | Laporta et al. | |
| 4,634,382 A | 1/1987 | Kusano et al. | |
| D291,731 S | 9/1987 | Aikins | |
| 4,759,768 A | 7/1988 | Hermann et al. | |
| 4,955,916 A | 9/1990 | Carignan et al. | |
| 4,969,909 A | 11/1990 | Barouk | |
| 5,047,059 A | 9/1991 | Saffar | |
| 5,092,896 A | 3/1992 | Meuli et al. | |
| 5,133,761 A | 7/1992 | Krouskop | |
| 5,179,915 A | 1/1993 | Cohen et al. | |
| 5,190,546 A | 3/1993 | Jervis | |
| 5,207,712 A | 5/1993 | Cohen | |
| 5,326,364 A | 7/1994 | Clift, Jr. et al. | |
| 5,405,400 A | 4/1995 | Linscheid et al. | |
| 5,405,401 A | 4/1995 | Lippincott, III et al. | |
| 5,425,777 A | 6/1995 | Sarkisian et al. | |
| 5,480,447 A | 1/1996 | Skiba | |
| 5,507,822 A | 4/1996 | Bouchon et al. | |
| 5,522,903 A | 6/1996 | Sokolow et al. | |
| 5,554,157 A * | 9/1996 | Errico et al. | 606/264 |
| 5,634,925 A * | 6/1997 | Urbanski | 606/264 |
| 5,674,297 A | 10/1997 | Lane et al. | |
| 5,702,472 A | 12/1997 | Huebner | |
| 5,725,585 A | 3/1998 | Zobel | |
| 5,782,927 A | 7/1998 | Klawitter et al. | |
| 5,876,434 A | 3/1999 | Flomenblit et al. | |
| 5,882,444 A | 3/1999 | Flomenblit et al. | |
| 5,951,288 A | 9/1999 | Sawa | |
| 5,958,159 A | 9/1999 | Prandi | |
| 5,984,970 A | 11/1999 | Bramlet | |
| 6,011,497 A | 1/2000 | Tsang et al. | |
| 6,017,366 A | 1/2000 | Berman | |
| 6,146,387 A | 11/2000 | Trott et al. | |
| 6,197,037 B1 | 3/2001 | Hair | |
| 6,200,330 B1 | 3/2001 | Benderev et al. | |
| 6,248,109 B1 | 6/2001 | Stoffella | |
| 6,319,284 B1 | 11/2001 | Rushdy et al. | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,423,097 B2 | 7/2002 | Rauscher | |
| 6,428,634 B1 | 8/2002 | Besselink et al. | |
| 6,454,808 B1 | 9/2002 | Masada | |
| 6,475,242 B1 | 11/2002 | Bramlet | |
| 6,699,247 B2 | 3/2004 | Zucherman et al. | |
| 6,699,292 B2 | 3/2004 | Ogilvie et al. | |
| 6,706,045 B2 * | 3/2004 | Lin et al. | 606/278 |
| 6,811,568 B2 | 11/2004 | Minamikawa | |
| 6,869,449 B2 | 3/2005 | Ball et al. | |
| 7,037,342 B2 | 5/2006 | Nilsson et al. | |
| 7,041,106 B1 * | 5/2006 | Carver et al. | 606/309 |
| 7,182,787 B2 | 2/2007 | Hassler et al. | |
| 7,240,677 B2 | 7/2007 | Fox | |
| 7,291,175 B1 | 11/2007 | Gordon | |
| 7,588,603 B2 | 9/2009 | Leonard | |
| 7,780,737 B2 | 8/2010 | Bonnard et al. | |
| 7,837,738 B2 | 11/2010 | Reigstad et al. | |
| 7,842,091 B2 | 11/2010 | Johnstone et al. | |
| 2001/0025199 A1 | 9/2001 | Rauscher | |
| 2002/0019636 A1 | 2/2002 | Ogilvie et al. | |
| 2002/0055785 A1 | 5/2002 | Harris | |
| 2002/0065561 A1 | 5/2002 | Ogilvie et al. | |
| 2002/0068939 A1 | 6/2002 | Levy et al. | |
| 2002/0082705 A1 | 6/2002 | Bouman et al. | |
| 2003/0040805 A1 | 2/2003 | Minamikawa | |
| 2003/0069645 A1 | 4/2003 | Ball et al. | |
| 2004/0093081 A1 | 5/2004 | Nilsson et al. | |
| 2004/0102853 A1 | 5/2004 | Boumann et al. | |
| 2004/0138756 A1 | 7/2004 | Reeder | |
| 2004/0220678 A1 | 11/2004 | Chow et al. | |
| 2005/0119757 A1 | 6/2005 | Hassler et al. | |
| 2005/0251265 A1 | 11/2005 | Calandruccio et al. | |
| 2005/0283159 A1 | 12/2005 | Amara | |
| 2006/0052725 A1 | 3/2006 | Santilli | |
| 2006/0052878 A1 | 3/2006 | Schmieding | |
| 2006/0074492 A1 | 4/2006 | Frey | |
| 2006/0084998 A1 | 4/2006 | Levy et al. | |
| 2006/0247787 A1 | 11/2006 | Rydell et al. | |
| 2007/0038303 A1 | 2/2007 | Myerson et al. | |
| 2007/0123993 A1 | 5/2007 | Hassler et al. | |
| 2007/0142920 A1 | 6/2007 | Niemi | |
| 2007/0185584 A1 | 8/2007 | Kaufmann et al. | |
| 2007/0213831 A1 | 9/2007 | de Cubber | |
| 2007/0239158 A1 | 10/2007 | Trieu et al. | |
| 2008/0039949 A1 | 2/2008 | Meesenburg et al. | |
| 2008/0154385 A1 | 6/2008 | Trail et al. | |
| 2008/0177262 A1 | 7/2008 | Augoyard | |
| 2008/0195219 A1 | 8/2008 | Wiley et al. | |
| 2008/0221697 A1 | 9/2008 | Graser | |
| 2008/0221698 A1 | 9/2008 | Berger | |
| 2008/0269908 A1 | 10/2008 | Warburton | |
| 2009/0254189 A1 | 10/2009 | Scheker | |
| 2009/0254190 A1 | 10/2009 | Gannoe et al. | |
| 2010/0010637 A1 | 1/2010 | Pequignot | |
| 2010/0016982 A1 | 1/2010 | Solomons | |
| 2010/0057214 A1 | 3/2010 | Graham et al. | |
| 2010/0121390 A1 | 5/2010 | Kleinman | |
| 2010/0131014 A1 | 5/2010 | Peyrot | |
| 2010/0131072 A1 | 5/2010 | Schulte | |
| 2010/0161068 A1 | 6/2010 | Lindner et al. | |
| 2010/0185295 A1 | 7/2010 | Emmanuel | |
| 2010/0249942 A1 | 9/2010 | Goswami et al. | |
| 2010/0256770 A1 | 10/2010 | Hakansson et al. | |
| 2010/0262254 A1 | 10/2010 | Lawrence et al. | |
| 2011/0004317 A1 | 1/2011 | Hacking et al. | |

FOREIGN PATENT DOCUMENTS

| | | | |
|---|---|---|---|
| FR | 2725126 A1 | 4/1996 | |
| FR | 2783702 A1 | 3/2000 | |
| FR | 2787313 A1 | 6/2000 | |
| FR | 2794019 A1 | 12/2000 | |
| FR | 2846545 A1 | 5/2004 | |
| FR | 2846545 B | 5/2004 | |
| FR | 2884406 | 10/2006 | |
| GB | 2119655 A | 11/1983 | |
| GB | 2430625 A | 4/2007 | |
| JP | 60145133 A | 7/1985 | |
| JP | 7303662 A | 11/1995 | |
| JP | 2004535249 A | 11/2004 | |
| JP | 2007530194 A | 11/2007 | |
| WO | 2005063149 A1 | 7/2005 | |
| WO | 2005104961 A1 | 11/2005 | |
| WO | WO 2006109004 A1 * | 10/2006 | |

OTHER PUBLICATIONS

International Search Report, PCT/FR2006/050345, dated Aug. 30, 2006.

* cited by examiner

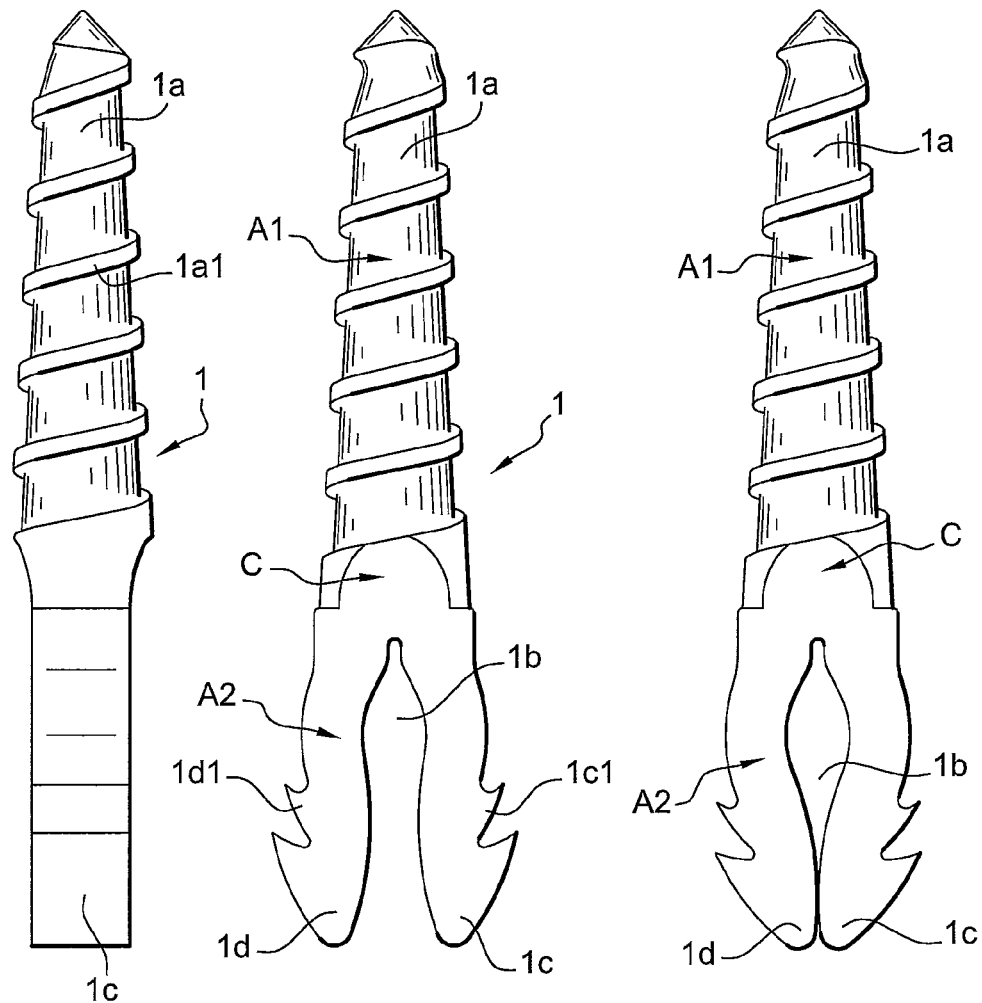

RESORPTIVE INTRAMEDULLARY IMPLANT BETWEEN TWO BONES OR TWO BONE FRAGMENTS

CROSS REFERENCE TO RELATED APPLICATIONS

This application is the US national phase of PCT application PCT/FR2009/051658, filed 2 Sep. 2009, published 18 Mar. 2010 as 2010/029246, and claiming the priority of French patent application 0856035 itself filed 9 Sep. 2008, whose entire disclosures are herewith incorporated by reference.

The invention relates to the technical field of orthopedic implants, particularly for arthrodesis and osteosynthesis.

More particularly, the invention relates to an intramedullary implant for arthrodesis between two bone parts or osteosynthesis between two bone fragments, particularly in the case of the hand or foot.

Different solutions have been proposed to achieve these functions.

For example, a solution comes from the teaching of patent application FR 2,884,406 [US 2008/0177262], of which the applicant of the present application is also the applicant. This patent describes an intramedullary osteosynthesis device constituted of an elongated body whose ends constitute anchor zones cooperating with the bone parts to be immobilized. The anchor zones are shaped and made of a material selected to enable insertion into the bone parts, then to ensure an anchor in the bone parts by preventing any rotational movement by resisting traction and by maintaining a compression force.

Another solution also comes from patent application FR 07.02003 [US 2010/0131014], also from the same applicant. This document describes an implant in the form of two anchor zones connected by a central zone and whose general shape is substantially inscribed in a very elongated rectangle of X-shape, so as to form in the anchor zones two legs adapted to move apart by elastic or shape-memory effect.

From this design, different criteria have been established to make the implant easy to place and efficient in order to create a primary and secondary stability for the osteosynthesis or arthrodesis site.

However, these solutions are not adapted for the case of an implant made of resorptive material.

From this state of the art, the object that the invention proposes to attain is further improving the anchor and the stability of the implant as well as its adaptation to the morphology of the implantation site when the implant is made of resorptive material.

To solve such a problem, a resorptive intramedullary implant between two bones or two bone fragments has been designed and developed; it is constituted, in a known manner, of a single-piece body having a general elongated shape with, at each end, zones for anchoring to the bone parts being considered. According to the invention, one of the zones has a cylindrical shape, whereas the other zone is flat.

Advantageously, the implant is made of a resorptive material whose mechanical properties are determined to last the time necessary for the consolidation, so that the implant is resorbed after six months. For example, the implant is composed of lactic acid polymer or copolymer (PLA, PGA . . . ).

Considering the specific mechanical characteristics of resorptive materials, and to solve the given problem of improving anchor and stability, the cylindrical cross-section is threaded and tapers in the direction of its free end.

To solve the given problem of enabling a deformation by elasticity, thus causing an expansion adapted to the geometry of the site and to the properties of the material, the flat cross-section zone has, substantially in its median portion, an opening adapted to enable elastic deformation of the zone. The opening defines at least two anchor arms.

It therefore appears that the combination of a cylindrical and threaded anchor zone and a flat-sectioned anchor zone is particularly advantageous considering the problem to be solved.

To solve the given problem of resisting the shear and flexion forces susceptible of occurring in the area of the bone site, between the two anchor zones, the body has a central zone of transition adapted to resist the shear and flexion forces occurring in the area of the bone site and adapted to serve as an abutment.

From this basic design of the implant, the anchor zones are either coaxial or angularly offset by between about 1° and 30° and, advantageously, by 10°. The bend between the anchor zones is located so as to substantially correspond to an arthrodesis line of the bones being considered.

The invention is explained in more detail hereinafter with reference to the attached drawings, in which:

FIG. 2 is a front view of the implant before insertion into the bone part in question;

FIG. 3 is a side view corresponding to FIG. 2;

FIG. 4 is a view like FIG. 2 showing the position of the anchor arms of the flat section after insertion;

The implant according to the invention has a one-piece body 1 of elongated shape and having a first proximal zone A1 and a second distal zone A2. The entire implant body is made of a resorptive material whose mechanical properties are determined for the implant to be resorbed in no less than about 6 months. In one embodiment, the implant is composed of lactic acid polymer or copolymer (PLA, PGA . . . ).

As will be described later in the description, the zones A1 and A2 have anchor formations for the respective bone parts. Taking into account the specific characteristics of the resorptive material and to attain the given object of anchor and stability, the zone A1 is of a cylindrical shape section whereas the other zone A2 is flat.

The zone A1 has a generally cylindrical outer surface 1a with a limited taper toward its free end. The surface 1a has a helical rib forming a screwthread 1a1.

The zone A2 is flat and has substantially in its center, an opening 1b adapted to enable elastic deformation of the zone A2. More particularly, the opening 1b defines at least two anchor arms 1c and 1d, each having at least one outwardly projecting tooth 1c1, 1d1.

Advantageously, between the two zones A1 and A2 the body 1 has a central zone C for transition adapted to resist shear and flexion forces that can occur at the end of a bone. By way of nonlimiting example, this median zone C can have a length of about 3.5 mm and a thickness of about 2 mm, for an overall implant length comprised between about 15 and 25 mm and a diameter of about 2 or 3 mm at the zone A1.

Figure 1:
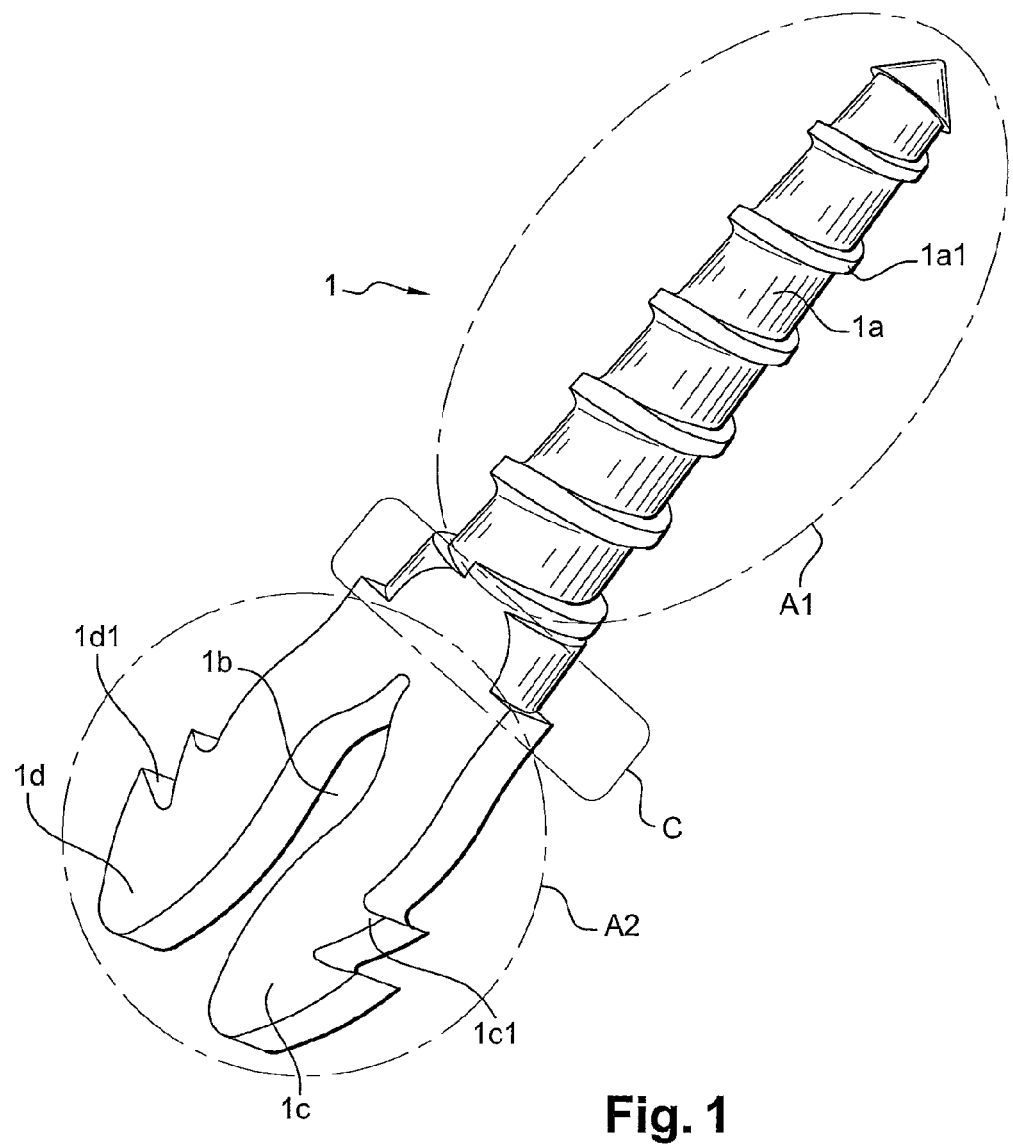
FIG. 1 is a perspective view of the implant.

In the embodiment shown in FIG. 1, the two zones A1 and A2 are coaxial.

Figure 5:
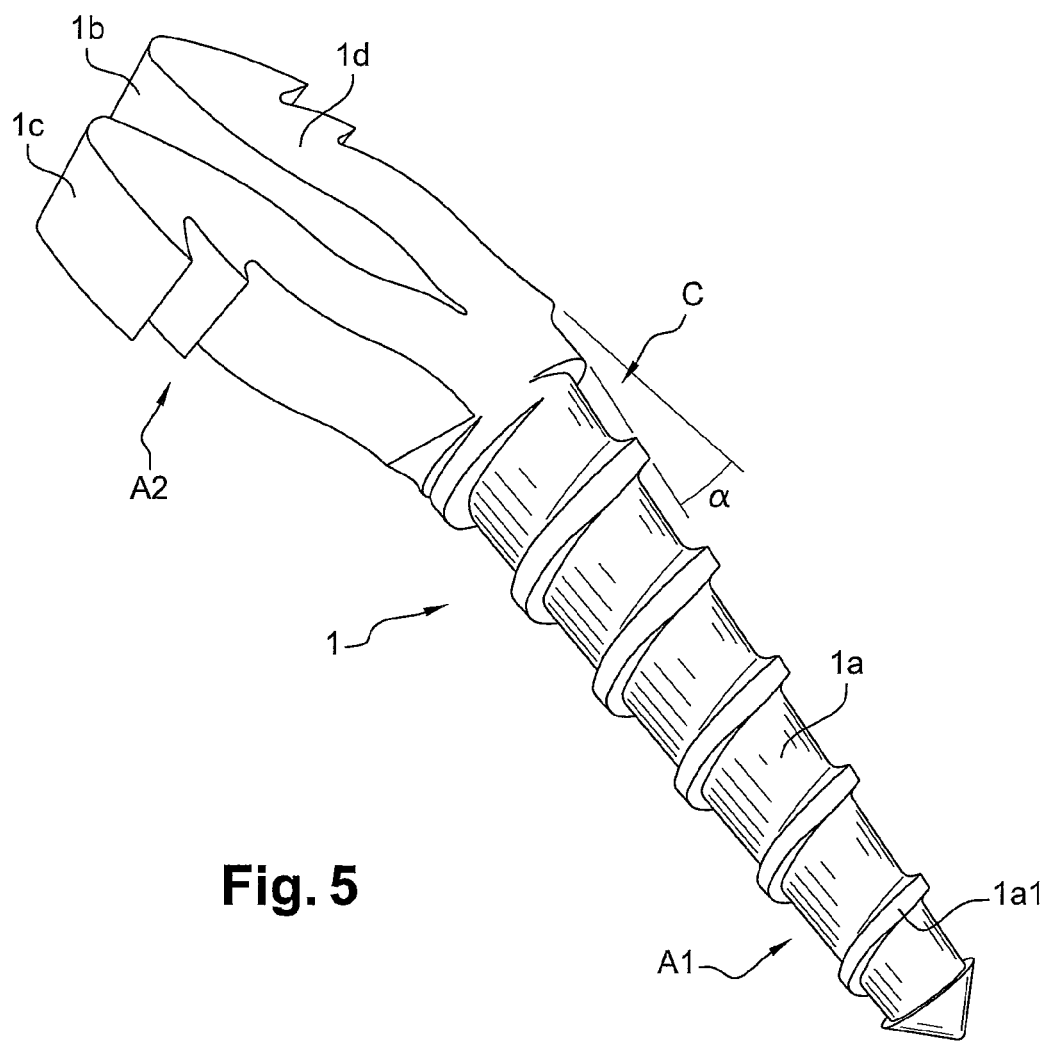
FIG. 5 is a perspective view of another advantageous embodiment of the implant.

To solve the problem of adaptation to the shape of the implantation site, the anchor zones A1 and A2 can be offset at an angle α adapted to the geometry of the bone site. This angle α is comprised between about 1° and 30° and, advantageously, on the order of 10° when the implant is for foot arthrodesis (FIG. 5).

In this embodiment in which the two anchor zones are angularly offset, the bend is located so as to correspond substantially to the arthrodesis line of the bone parts being fused.

Figure 6:
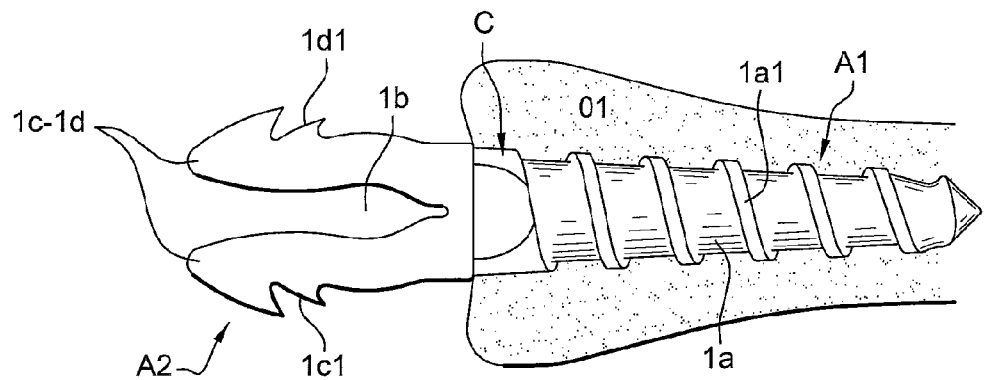
FIGS. 6 and 7 show the installation of the implant into two bone parts.
Figure 7:
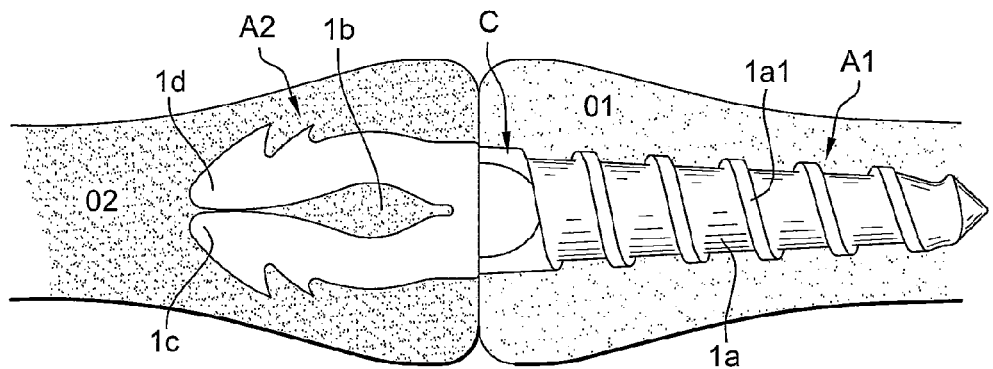

FIGS. 6 and 7 schematically show the positioning of the implant according to the invention between two bone parts O1 and O2. After suitable holes have been made in the bone by a rasp-type tool, the operator screws the thread 1a into the bone part O1 substantially up to the median zone C that serves as abutment preventing the implant from sinking too deeply into the bone (FIG. 6). The operator then fits the second bone part O2 back onto the anchor arms 1d and 1c of the zone A2, the anchor arms then spread and tighten by elasticity (FIG. 7).

The operative technique can be the following:
Drilling of the two holes with a conventional drill;
Preparation of the holes with a rasp for the flat side and a bone tap to form the inner screw thread on the cylindrical side;
Use of a screwdriver with a gripper end;
Screwing in the cylindrical side P1 [A1] for an arthrodesis IPP of the foot;
Fitting of the bone back onto the flat side [A2] of the implant.

The advantages are readily apparent from the description; in particular, it is to be emphasized and understood that the combination of the two anchor zones A1 and A2 of cylindrical and a flat shape, respectively, significantly enhances anchor and stability of the implant adapted to the geometry of the bone site and to the material properties, namely, a resorptive material.

The invention claimed is:

1. An intramedullary implant for use between two bones or bone fragments, the implant comprising:
a one-piece body having an elongated shape, the body having opposing first and second ends, each of the ends having a longitudinal axis therethrough and an anchor zone for anchoring to a respective bone part,
wherein the anchor zone of the first end is threaded and has a generally cylindrical shape and the anchor zone of the second end has a flat cross-section in a direction perpendicular to the longitudinal axis thereof, and
wherein the anchor zone of the second end has a plurality of outwardly projecting teeth forming a portion of the flat cross-section thereof, at least a first tooth of the plurality of teeth being spaced from a second tooth of the plurality of teeth in a direction along the longitudinal axis of the second end, and at least the first tooth facing in a direction opposite a third tooth of the plurality of teeth and the second tooth facing in a direction opposite a fourth tooth of the plurality of teeth.

2. The implant according to claim 1, wherein the zone of flat cross-section has substantially in its median portion an opening adapted to allow elastic deformation of the flat zone.

3. The implant according to claim 2, wherein the opening defines at least two anchor arms.

4. The implant according to claim 1 wherein, the body has a central transition zone between the two anchor zones adapted to resist shear and flexion forces occurring in the area of the bone site, the central transition zone including a step having a face defining a plane perpendicular to the longitudinal axis of the first end adapted to serve as an abutment preventing overinsertion of the implant into the respective bone part.

5. The implant according to claim 1 wherein the anchor zones are coaxial.

6. The implant according to claim 1, wherein the anchor zones are angularly offset.

7. The implant according to claim 6, wherein the anchor zones are angularly offset by between 1° and 30°.

8. The implant according to claim 6 wherein the angular offset between the anchor zones is located so as to correspond substantially to an arthrodesis line of the bones being considered.

9. The implant according to claim 1 wherein the body is adapted to be elastically deformed.

10. The intramedullary implant according to claim 1, wherein the body is made of resorptive material.

11. The implant according to claim 1, wherein the entire anchor zone of the first end tapers in a direction along the longitudinal axis thereof away from the second end.

12. An intramedullary implant for use between two bone parts, the implant having an elongated one-piece body with:
one end of generally cylindrical shape and having an external screwthread;
an opposite end formed as a split flat metal bar having two spreadable and elastically deformable legs;
a longitudinal axis extending through the end of generally cylindrical shape; and
a step having a flat face defining a plane perpendicular to the longitudinal axis and forming an abutment between the opposing ends, the abutment adapted to prevent overinsertion of the end of generally cylindrical shape into the respective bone part.

13. The intramedullary implant according to claim 12, wherein the body is made of resorptive material.

14. The implant according to claim 12, wherein the ends are angularly offset.

15. The implant according to claim 12, wherein the one end of generally cylindrical shape tapers in a direction away from the opposite end.

16. An intramedullary implant for use between two bones or bone fragments, the implant comprising:
a one-piece body having an elongated shape, the body having (i) opposing first and second ends, each of the ends having a longitudinal axis and an anchor zone for anchoring to a respective bone part, and (ii) a step having a flat face defining a plane perpendicular to the longitudinal axis of the first end and forming an abutment between the anchor zones of the first and second ends, the abutment preventing overinsertion of the anchor zone into the respective bone or bone fragment,
wherein the anchor zone of the first end is threaded and has a generally cylindrical shape and the anchor zone of the second end has a flat cross-section in a direction perpendicular to the longitudinal axis thereof, and wherein the anchor zone of the second end has a plurality of outwardly projecting teeth forming a portion of the flat cross-section thereof, at least a first tooth of the plurality of teeth being spaced from a second tooth of the plurality of teeth along the longitudinal axis of the first end, and at least the first tooth facing in a direction opposite a third tooth of the plurality of teeth and the second tooth facing in a direction opposite a fourth tooth of the plurality of teeth.

17. The implant according to claim 16, wherein the anchor zone of the second end includes at least two anchor arms, the arms being elastically deformable relative to each other.

18. The implant according to claim 16, wherein the body is made of resorptive material.

* * * * *